United States Patent [19]

Kuroda et al.

[11] 4,418,018

[45] Nov. 29, 1983

[54] PROCESS FOR THE PRODUCTION OF 2,3-DICHLOROPROPIONITRILE

[75] Inventors: Kazuyuki Kuroda; Riyoiti Ikematsu; Kazunari Nitta, all of Ohmuta, Japan

[73] Assignee: Mitsui Toatsu Chemicals, Inc., Tokyo, Japan

[21] Appl. No.: 342,804

[22] Filed: Jan. 26, 1982

[30] Foreign Application Priority Data

Feb. 5, 1981 [JP] Japan ................... 56-15024

[51] Int. Cl.$^3$ ................... C07C 120/00; C07C 121/16
[52] U.S. Cl. ................... 260/465.7
[58] Field of Search ................... 260/465.7

[56] References Cited

U.S. PATENT DOCUMENTS 4,350,643  9/1982  Nagai et al. ................... 260/465.7

OTHER PUBLICATIONS

Journal of Organic Chemistry, Lorette, vol. 26 (1961), pp. 2324-2327.
Journal of General Chemistry of the USSR, Ivanov et al, vol. 28, (1958).
Brintzinger, et al.; Angew, Chem., A, 60, 311-312, (1948).

Primary Examiner—Joseph Paul Brust
Attorney, Agent, or Firm—Fisher, Christen & Sabol

[57]  ABSTRACT

In a process for the production of 2,3-dichloropropionitrile by the chlorination of acrylonitrile, the improvement which comprises chlorinating acrylonitrile in the presence of pyridine or an alkylpyridine in combination with an alkaline earth metal carbonate.

6 Claims, No Drawings

PROCESS FOR THE PRODUCTION OF 2,3-DICHLOROPROPIONITRILE

BACKGROUND OF THE INVENTION

1. Field of the Invention

This invention relates to a commercially advantageous process for the production of 2,3-dichloropropionitrile. More specifically, this invention pertains to a process for the production of 2,3-dichloropropionitrile by chlorinating acrylonitrile with chlorine in the liquid phase in the presence of pyridine or an alkylpyridine in combination with an alkaline earth metal carbonate.

2. Description of the Prior Art 2,3-Dichloropropionitrile is an industrially useful compound that finds application as a raw material for polymeric compounds, amino acids, agricultural chemicals, medicines, etc.

A usual process for the production of 2,3-dichloropropionitrile comprises blowing chlorine gas into a liquid phase containing acrylonitrile in the presence of a catalyst, and purifying the resulting reaction mixture by distillation. Inorganic catalysts such as sodium bicarbonate and sodium hydrogen phosphate or organic catalysts such as pyridine, quinoline and dimethyl formamide are known as catalysts useful in this process. In commercial practice, the use of an organic catalyst, especially pyridine is advantageous.

Production of 2,3-dichloropropionitrile by the chlorination of acrylonitrile in the liquid phase using pyridine as a catalyst is described, for example, in Angew. Chem., A, 60, 311 (1948), Zhur. Obshch. Khim, 28, 139 (1958), and Journal of Organic Chemistry, 26, 2324 (1961).

These known processes, however, give rise to various problems in commercial practice because unless expensive pyridine is used in an amount of as large as about 15 to 30% by weight based on acrylonitrile, an abrupt exothermic phenomenon occurs and 2,3-dichloropropionitrile cannot be obtained. For example, according to the known processes, pyridine is present in a high concentration in the reaction solution after the reaction, and therefore, distillation by heating of the reaction solution as obtained results in the dehydrochlorination of 2,3-dichloropropionitrile. If, in an attempt to prevent the dehydrochlorination reaction, the reaction solution is washed prior to distillation to remove pyridine, a part of the 2,3-dichloropropionitrile together with the unreacted acrylonitrile dissolves in the water layer, and the yield of 2,3-dichloropropionitrile is reduced. An additional serious problem is that the disposal of the waste water which gives off an offensive odor by the inclusion of pyridine becomes difficult.

It is an object of this invention therefore to provide a novel process for the production of 2,3-dichloropropionitrile, which is industrially advantageous in that the amount of the pyridine-type catalyst used is extremely small and the reaction solution needs not to be washed with water before distillation.

The present inventors have found that if a specified amount of an alkaline earth metal carbonate is used together with pyridine or an alkylpyridine in the above process, the amount of the pyridine or alkylpyridine used can be drastically reduced without a decrease in the yield of 2,3-dichloropropionitrile as compared with the known processes in which pyridine is used alone.

SUMMARY OF THE INVENTION

Thus, according to this invention, there is provided a process for the production of 2,3-dichloropropionitrile which comprises chlorinating acrylonitrile with chlorine in the liquid phase in the presence of pyridine or an alkylpyridine in combination with an alkaline earth metal carbonate. This process is very advantageous both economically and operationally because the amount of the expensive pyridine or alkylpyridine is extremely small, and consequently, the work-up of the reaction solution after the reaction is simple.

DETAILED DESCRIPTION OF THE INVENTION

The amount of pyridine or the alkylpyridine used in this invention as a catalyst is from 0.3 to 15% by weight based on the weight of acrylonitrile. If it is less than 0.3% by weight, the rate of the reaction decreases beyond a practical level. If it is larger than 15% by weight, no problem arises in the reaction, but no economic advantage over the prior art can be obtained. The especially desirable amount of the pyridine or alkylpyridine is 1 to 10% by weight based on the weight of acrylonitrile. Examples of suitable alkylpyridines include methylpyridine, ethylpyridine, dimethylpyridine, diethylpyridine and ethylmethylpyridine. These catalytic compounds may be used singly or as a mixture of two or more.

Examples of the alkaline earth metal carbonate used in combination with pyridine or the alkylpyridine in the process of this invention are beryllium carbonate, magnesium carbonate, calcium carbonate, strontium carbonate, barium carbonate and a mixture of two or more of these compounds. Magnesium carbonate, calcium carbonate and barium carbonate, especially calcium carbonate, are industrially advantageous because of their low cost and ready availability.

In the process of this invention, the amount of the alkaline earth metal carbonate is of great significance. When the amount of the pyridine or the alkylpyridine used is smaller than in the prior art and no alkaline earth metal carbonate is used or the amount of the carbonate is less than the suitable amount, an abrupt exotherm occurs during the chlorinating reaction to give undesirable by-products such as 3-chloropropionitrile and 2,3,3-trichloropropionitrile. The amount of the alkaline earth metal carbonate required is at least 1% by weight, preferably at least 3% by weight, based on the weight of acrylonitrile. There is no particular upper limit to the amount of the alkaline earth metal carbonate; it is properly determined for economic or operational reasons (if the amount of the alkaline earth metal carbonate is too large, the reaction solution becomes a concentrated slurry, and the operation becomes difficult).

The reaction temperature at which acrylonitrile is chlorinated by the process of this invention is 10° to 60° C., preferably 20° to 50° C. If the reaction temperature is lower than 10° C., the rate of the reaction decreases, and the ratio of chlorine which dissipates out of the system unreacted increases. When the reaction temperature is higher than 60° C., undesirable phenomena, such as the increased production of tarry-substances as by-products, tend to occur.

A desirable reaction apparatus for use in the process of the invention is an acid-resistant reaction apparatus equipped with a stirrer, a thermometer, a chlorine-blowing tube, a reflux condenser and a cooling jacket or coil.

Since the reaction in the process of this invention is exothermic, the rate of introduction of chlorine can be properly selected depending upon the ability of the reaction apparatus to remove heat. When the ability of the apparatus to remove heat is great, it is possible to increase the rate of introducing chlorine and thus shorten the reaction time. If the heat-removing ability is low, the rate of introduction of chlorine may be adjusted such that a predetermined reaction temperature can be maintained. Usually, the time required for the reaction is several hours to several tens of hours. In order to complete the reaction substantially, chlorine is introduced usually in an amount of about 1 to about 1.5 moles per mole of acrylonitrile although the amount may vary depending upon the reaction temperature. The end point of chlorine introduction can easily be judged as the point at which the temperature of the reaction solution becomes identical with that of the cooling water. After a predetermined amount of chlorine has been introduced, the reaction system may be stirred further at a predetermined temperature in order to effectively utilize the unreacted chlorine dissolved therein. By so doing, it is possible to lower the concentration of the unreacted acrylonitrile in the reaction solution. Chlorine used in the process of this invention need not be of particularly high purity. For example, chlorine obtained by usual electrolysis of an aqueous solution of sodium chloride may be directly used. The process of this invention gives quite the same results whether it is carried out under light irradiation or under shielding of light.

After the chlorination reaction, nitrogen, argon, air or the like is passed into the reaction solution to remove the unreacted chlorine remaining in a trace amount, and the alkaline earth metal carbonate is separated by filtration. Distillation of the filtrate by heating gives 2,3-dichloropropionitrile of high purity. An equivalent result is obtained by removing the unreacted chlorine and distilling the reaction solution containing the alkaline earth metal carbonate by heating. In either case, pyridine or the alkylpyridine does not distill out, but remains in the distillation still forming an odorless adduct with a small amount of 2,3-dichloropropionitrile. The distillation residue containing pyridine is either incinerated, or to recovery pyridine, subjected to an alkali treatment.

It is apparent from the above detailed description that the process of this invention can give 2,3-dichloropropionitrile with economic and operational advantages over the prior processes by chlorinating acrylonitrile in the presence of a very small amount of pyridine or an alkylpyridine and an inexpensive alkaline earth metal carbonate.

The following non-limitative examples specifically illustrate the present invention.

EXAMPLE 1

A cylindrical flask equipped with a chlorine-introducing tube, a thermometer, a reflux condenser, a stirrer and a cooling jacket was charged with 159.3 g of acrylonitrile, 3.0 g of pyridine and 5.0 g of calcium carbonate, and the entire apparatus was shielded from light. Then, with stirring, chlorine was introduced into the flask over 10 hours at a rate of 140 ml per minute. During this time, the reaction temperature was maintained at 30° C. by adjusting the temperature of the cooling water. After the introduction of chlorine, the mixture was stirred further at 30° C. for 2 hours, and then nitrogen was passed through the reaction solution at a rate of 180 ml per minute for 2 hours to remove the unreacted chlorine out of the reaction system. The reaction mixture was filtered to remove calcium carbonate. The filtrate was distilled under reduced pressure to give 339.0 g of a fraction having a boiling point of 61° C./13 mmHg. Gas-chromatographic analysis showed this fraction to be 2,3-dichloropropionitrile completely free from impurities. The yield of the product based on acrylonitrile was 91.2%. The amount of the distillation residue was about 9 g.

COMPARATIVE EXAMPLE

The same reactor as used in Example 1 was charged with 159.3 g of acrylonitrile and 3.0 g of pyridine, and the entire reactor was shielded from light. While the temperature of the inside of the reactor was maintained at 30° C., chlorine was introduced at a rate of 225 ml per minute with stirring. In about 2 hours and 15 minutes after the start of chlorine introduction (at which point the mole ratio of chlorine to acrylonitrile was about 0.4), an abrupt exothermic phenomenon occurred, and the temperature of the inside of the reactor rose to about 47° C. The inside temperature the reactor was then lowered to 30° C., and chlorine was further introduced for 4 hours and 15 minutes at a rate of 225 ml per minute (the total time of chlorine introduction was 6.5 hours). Then, the mixture was stirred at 30° C. for 2 hours. Subsequently, with stirring, nitrogen was passed through the reaction solution for 1 hour at a rate of 180 ml per minute to remove the unreacted chlorine. Thus, 424.5 g of a reaction solution was obtained. Gas-chromatographic analysis showed that 2,3-dichloropropionitrile was not formed at all, and the reaction product consisted mostly of 3-chloropropionitrile and 2,2,3-trichloropropionitrile.

EXAMPLE 2

The same reaction as in Example 1 was followed except that methylpyridine (a mixture of 2-, 3-, and 4-methylpyridines) was used instead of pyridine. There was obtained 332.0 g of 2,3-dichloropropionitrile in a yield, based on acrylonitrile, of 89.3%. The amount of the distillation residue was about 10 g.

What we claim is:

1. In a process for the production of 2,3-dichloropropionitrile by the chlorination of acrylonitrile, the improvement which comprises chlorinating acrylonitrile at a temperature of 10° to 60° C. using a chlorine gas in the presence of 0.3 to 15% by weight, based on acrylonitrile, of pyridine or an alkylpyridine and at least 1.0% by weight, based on acrylonitrile, of an alkaline earth metal carbonate.

2. The process of claim 1, wherein the amount of pyridine or alkylpyridine is from 1 to 10% by weight based on acrylonitrile.

3. The process of claim 1, wherein the alkaline earth metal carbonate is calcium carbonate.

4. The process of claim 1, wherein the alkylpyridine is methylpyridine.

5. The process of claim 1, wherein the reaction temperature is from 20° to 50° C.

6. The process of claim 1, wherein the alkylpyridine is substituted with an alkyl group having 1-5 carbon atoms.

* * * * *